(12) United States Patent
Murthy (10) Patent No.: US 7,973,022 B2
(45) Date of Patent: Jul. 5, 2011

(54) FLUOROQUINOLONE CARBOXYLIC ACID SALT COMPOSITIONS

(75) Inventor: Yerramilli V. S. N. Murthy, Apex, NC (US)

(73) Assignee: IDEXX Laboratories, Inc., Westbrook, ME (US)

( * ) Notice: Subject to any disclaimer, the term of this patent is extended or adjusted under 35 U.S.C. 154(b) by 1033 days.

(21) Appl. No.: 11/723,841

(22) Filed: Mar. 22, 2007

(65) Prior Publication Data

US 2007/0203097 A1 Aug. 30, 2007

Related U.S. Application Data

(63) Continuation-in-part of application No. 11/700,174, filed on Jan. 31, 2007.

(60) Provisional application No. 60/774,267, filed on Feb. 17, 2006.

(51) Int. Cl.
*A01N 43/04* (2006.01)
*A61K 31/715* (2006.01)
*A61K 31/497* (2006.01)
*A61K 31/47* (2006.01)

(52) U.S. Cl. ............... 514/58; 514/253.08; 514/312

(58) Field of Classification Search ............ None
See application file for complete search history.

(56) References Cited

U.S. PATENT DOCUMENTS

| | | | |
|---|---|---|---|
| 4,238,308 A | 12/1980 | Kocache et al. | |
| 4,292,317 A | 9/1981 | Pesson | |
| 4,448,962 A | 5/1984 | Irikura et al. | |
| 4,499,091 A | 2/1985 | Wentland et al. | |
| 4,668,784 A | 5/1987 | Mascellani et al. | |
| 4,704,459 A | 11/1987 | Todo et al. | |
| 4,795,751 A | 1/1989 | Matsumoto et al. | |
| 5,464,796 A | 11/1995 | Petersen et al. | |
| 5,476,854 A | 12/1995 | Young | |
| 5,484,785 A | 1/1996 | Yeon et al. | |
| 5,532,239 A | 7/1996 | Pruna | |
| 5,756,506 A * | 5/1998 | Copeland et al. | 514/254.11 |
| 5,912,255 A | 6/1999 | Bussell | |
| 5,998,418 A * | 12/1999 | Bonse et al. | 514/253.08 |
| 6,017,912 A | 1/2000 | Bussell | |
| 6,262,072 B1 | 7/2001 | Lee et al. | |
| 6,383,471 B1 | 5/2002 | Chen et al. | |
| 6,482,823 B1 | 11/2002 | Yu et al. | |
| 6,822,098 B2 | 11/2004 | Kazami et al. | |
| 6,825,199 B2 | 11/2004 | Damagala et al. | |
| 6,887,487 B2 | 5/2005 | Murthy et al. | |
| 6,911,442 B1 | 6/2005 | Davies et al. | |
| 2004/0176321 A1 * | 9/2004 | Saoji et al. | 514/58 |

FOREIGN PATENT DOCUMENTS

| | | |
|---|---|---|
| BE | 870576 | 3/1979 |
| BE | 887574 | 6/1981 |
| DE | 3142854 | 5/1983 |
| EP | 047005 | 11/1984 |
| EP | 140116 | 5/1988 |
| EP | 078362 | 2/1989 |
| EP | 131839 | 2/1989 |
| EP | 154780 | 4/1990 |
| EP | 221463 | 8/1991 |
| EP | 520240 | 6/1992 |
| EP | 206283 | 1/1993 |
| EP | 310849 | 3/1993 |

OTHER PUBLICATIONS

Olivera, et al., Ototopical ciprofloxacin in a glycerin vehicle for the treatment of acute external otitis, 2004, Ear, Nose, Throat Journal, vol. 83, pp. 625-638, Abstract.

Teng, et al., Pharmacokinetics of Trovafloxacin (CP-99,219), a New Quinolone, in Rats, Dogs, and Monkeys, 1996, Antimicrobial Agents and Chemotherapy, vol. 40, pp. 561-566, Materials and Methods.

* cited by examiner

*Primary Examiner* — Traviss C McIntosh, III (74) *Attorney, Agent, or Firm* — Kilpatrick Townsend & Stockton LLP (57) ABSTRACT

The invention relates to pharmaceutical compositions that are a solution of a salt formed between a fluoroquinolone and a carboxylic acid, a cyclodextrin, and a pharmaceutically acceptable organic solvent and to methods of treating a condition in an animal by administering to an animal in need thereof the pharmaceutical composition of the invention.

23 Claims, 2 Drawing Sheets

FLUOROQUINOLONE CARBOXYLIC ACID SALT COMPOSITIONS

CROSS REFERENCE TO RELATED APPLICATIONS

This application is a continuation-in-part of application Ser. No. 11/700,174, filed Jan. 31, 2007, which claims the benefit of U.S. provisional application Ser. No. 60/774,267, filed Feb. 17, 2006, the contents of which are expressly incorporated herein.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

FIELD OF THE INVENTION

The invention relates to fluoroquinolone containing pharmaceutical compositions and to methods of treating a condition in an animal by administering to an animal in need thereof the pharmaceutical composition of the invention. The pharmaceutical compositions are a solution comprising a salt formed between a fluoroquinolone and a carboxylic acid, a cyclodextrin, and a pharmaceutically acceptable organic solvent. The fluoroquinolone containing pharmaceutical compositions can be administered orally or by injection.

BACKGROUND OF THE INVENTION

The following discussion of the background of the invention is merely provided to aid the reader in understanding the invention and is not admitted to describe or constitute prior art to the present invention.

Fluoroquinolones are antibiotics used to treat infections caused by microorganisms. Fluoroquinolones have the basic structure shown below:

wherein $R_1$, $R_2$, $R_3$, and $R_4$ can be a variety of functional groups and X can be carbon or a variety of heteroatoms either of which may be substituted or unsubstituted.

Fluoroquinolones were first developed in the early 1960s. The first fluoroquinolone, nalidixic acid, was approved by the FDA in 1963 for the treatment of urinary tract infections. Nalidixic acid is rapidly absorbed after oral administration and is excreted into the urine in bactericidal concentrations. Nalidixic acid, however, has several limitations that prevents its use in other types of infections. Specifically, nalidixic acid has a narrow spectrum of activity and microorganisms easily developed resistance to the drug. The development of other fluoroquinolones by chemically altering the basic structure of nalidixic acid, however, has led to improved fluoroquinolone that are more effective against resistant bacteria and effective against a broader range of bacteria.

Representative fluoroquinolones include, but are not limited to, those described in BE 870,576, U.S. Pat. No. 4,448,962, DE 3,142,854, EP 047,005, EP 206,283, BE 887,574, EP 221,463, EP 140,116, EP 131,839, EP 154,780, EP 078,362, EP 310,849, EP 520,240, U.S. Pat. No. 4,499,091, U.S. Pat. No. 4,704,459, U.S. Pat. No. 4,795,751, U.S. Pat. No. 4,668,784, and U.S. Pat. No. 5,532,239.

The fluoroquinolone class of antibiotics are a powerful tool in combating bacterial infections. Fluoroquinolones have been used extensively to treat respiratory tract infections (including for example, bronchitis, pneumonia, tuberculosis), urinary tract infections, diarrhea, postoperative-wound infections, bone and joint infections, skin infections, inflammation of the prostate, ear infections, various sexually transmitted diseases, various infections that affect people with AIDS, and other conditions, in animals and humans. Fluoroquinolone are active against a wide spectrum of gram-positive and gram-negative bacteria. For example, various fluoroquinolones have been found to be effective against *Staphylococcus aureus*, *Streptococcus pneumoniae*, coagulese-negative *staphylococci*, *Streptococcus pyogenes*, *Staphylococcus epidermis*, *Pseudomonas aeruginosa*, *Escherichia coli*, *Klebsiella pneumoniae*, *Enterobacter cloacae*, *Proteus mirabilis*, *Proteus vulgaris*, *Providencia stuartii*, *Morganella morganii*, *Citrobacter diversus*, *Citrobacter freundii*, *Haemophilus influenzae*, and *Neisseria gonorrhea*, and other organisms. Indeed, the mounting resistance of *Staphylococcus aureus* to both penicillin and erythromycin has made the fluoroquinolone antibiotics a viable alternative for the treatment of skin diseases.

The mode of action of fluoroquinolones is to target DNA gyrase in the bacteria and interfere with bacterial replication.

Fluoroquinolones can be administered orally, topically, or parenterally.

U.S. Pat. No. 5,476,854 describes the oral, intravenous, and transdermal use of lomefloxacin to treat urinary tract infections, upper respiratory tract infections, sexually-transmitted infections, opthalmological infections, and intestinal infections.

U.S. Pat. No. 6,017,912 discloses a method of topically treating bacterial infections of the skin caused by susceptible organisms that comprises administering to an individual a composition of a fluoroquinolone antibiotic in a vehicle containing acetone and alcohol, applied directly to the affected areas of the human skin.

U.S. Pat. No. 5,912,255 discloses a pharmaceutical composition comprising a fluoroquinolone and benzoyl peroxide in a vehicle. The compositions are useful for the topical treatment of a variety of skin conditions.

U.S. Pat. No. 5,756,506 discloses a method of treating animals with fluoroquinolones by administering to the animal a single high dose of the fluoroquinolone to replace multiple lower doses.

U.S. Pat. No. 5,532,239 discloses treating nephrotic syndromes with fluoroquinolone derivatives.

U.S. Pat. No. 6,887,487 discloses compositions comprising a salt of a pharmacologically active compound and a lipophilic counterion and a pharmaceutically acceptable water soluble solvent combined together to form an injectable composition. The patent also discloses methods of treating a mammal with the disclosed compositions.

U.S. Pat. No. 5,484,785 discloses 1-cyclopropyl-6-fluoro-1,4-dihydro-4-oxo-7-(1-piperazinyl)-quinoline-3-carboxylic acid 5-oxotetrahydrofuran-2-carboxylate or 2-hydroxyglutarate and processes for making the same.

U.S. published application no. 2005/0049210 discloses composition for the administration of a pharmacologically active compound to a mammal comprising: a salt of the pharmacologically active compound with a lipophilic counterion; and a pharmaceutically acceptable, water immiscible solvent; combined together to form a composition that releases the active compound over time when administered to the mammal. The published application also discloses methods of treating a mammal with the disclosed compositions.

Solid oral pharmaceutical compositions, such as tablets and capsules, can be difficult for some individuals to swallow. For example, pediatric patients often find it difficult to swallow solid oral pharmaceutical compositions. Furthermore, solid oral pharmaceutical compositions can be difficult to administer to animals, such as cats. Thus, in many instances, liquid oral pharmaceutical compositions, such as solutions and suspensions, are desirable because they are easier to administer. Fluoroquinolones, however, are difficult to dissolve in aqueous liquids. Accordingly, there is a need in the art for new liquid fluoroquinolone compositions that can be more easily administered to animals.

The difficulty in dissolving fluoroquinolones in aqueous solutions also makes it difficult to develop fluoroquinolone compositions that are suitable for injection.

Citation of any reference in this section of this application is not to be construed that such reference is prior art to the present application.

SUMMARY OF THE INVENTION

The present invention relates to a pharmaceutical composition comprising a (i) a salt formed between a fluoroquinolone and a carboxylic acid, (ii) a cyclodextrin, and (iii) a pharmaceutically acceptable organic solvent, wherein the pharmaceutical composition is a solution. The invention further relates to a method of treating or preventing a condition in an animal comprising orally administering to the animal a pharmaceutical composition of the invention. The invention further relates to a method of treating or preventing a condition in an animal comprising administering to the animal a pharmaceutical composition of the invention by injection.

The invention further relates to a pharmaceutical composition comprising a fluoroquinolone in a solution, wherein the in-vivo bioavailability of the fluoroquinolone determined after an amount of the fluoroquinolone is administered orally to an animal as the pharmaceutical composition is substantially similar to the in-vivo bioavailability of the fluoroquinolone determined after the same amount of the fluoroquinolone is administered orally to an animal as a tablet.

DETAILED DESCRIPTION OF THE INVENTION

The invention relates to a pharmaceutical composition comprising (i) a salt formed between a fluoroquinolone and a carboxylic acid, (ii) a cyclodextrin, and (iii) a pharmaceutically acceptable organic solvent, wherein the pharmaceutical composition is a solution.

The invention further relates to a method of treating a condition in an animal comprising orally administering to the animal a pharmaceutical composition of the invention.

The invention further relates to a method of treating a condition in an animal comprising administering to the animal a pharmaceutical composition of the invention by injection.

The invention further relates to a pharmaceutical composition comprising a fluoroquinolone in a solution, wherein the in-vivo bioavailability of the fluoroquinolone determined after an amount of the fluoroquinolone is administered orally to an animal as the pharmaceutical composition is substantially similar to the in-vivo bioavailability of the fluoroquinolone determined after the same amount of the fluoroquinolone is administered orally to an animal as a tablet.

Definitions

The phrases "salt formed between a fluoroquinolone and a carboxylic acid" or "carboxylic acid salt of a fluoroquinolone," as those phrases are used herein, means the salt formed between a carboxylic acid and a fluoroquinolone.

The term "fluoroquinolone," as used herein, means any compound having the basic structure:

wherein $R_1$, $R_2$, $R_3$, and $R_4$ can be a variety of functional groups and X can be carbon, which may be substituted or unsubstituted, or nitrogen. One skilled in the art would readily recognize fluoroquinolones useful in the compositions and methods of the invention. Typically, the fluoroquinolones are useful as antibiotics but they may also be used to treat other conditions (for example, nephrotic syndromes).

The term "carboxylic acid," as used herein, means a carboxylic acid of formula R—C(O)OH, wherein R is a $C_1$-$C_4$ hydrocarbon group. In one embodiment, R is a $C_1$-$C_3$ hydrocarbon group. In one embodiment, R is a $C_1$ hydrocarbon group, i.e., the carboxylic acid is acetic acid. In one embodiment, the $C_1$-$C_4$ hydrocarbon group is substituted with an —OH group or a —NH$_2$ group.

The phrase a "$C_1$-$C_4$ hydrocarbon group," as used herein means a straight or branched, saturated or unsaturated, cyclic or non-cyclic, carbocyclic group having from 1 to 4 carbon atoms. Similarly, the phrases a "$C_1$-$C_3$ hydrocarbon group"

means a straight or branched, saturated or unsaturated, cyclic or non-cyclic, carbocyclic group having from 1 to 3 carbon atoms.

The term "salt," as used herein, means two compounds that are not covalently bound but are chemically bound by ionic interactions.

The term "solution," as used herein, means a uniformly dispersed mixture at the molecular or ionic level of one or more solid or liquid substances (solute) in one or more other liquid substances (solvent). The term "solution" is well known to one of ordinary skill in the art.

The phrase "substantially free of," as used herein, means less than about 5 percent by weight. For example, the phrase "a pharmaceutical composition substantially free of water" means that the amount of water in the pharmaceutical composition is less than about 5 percent by weight of the pharmaceutical composition.

The phrase "substantially similar to," as used herein means with ±20 percent of another value. For example, the phrase "the in-vivo bioavailability of the fluoroquinolone determined after an amount of the fluoroquinolone is administered orally to an animal as the liquid pharmaceutical composition is substantially similar to the in-vivo bioavailability of the fluoroquinolone determined after an amount of the fluoroquinolone is administered orally to an animal as a tablet" means that the in-vivo bioavailability of the fluoroquinolone determined after an amount of the fluoroquinolone is administered orally to an animal as the liquid pharmaceutical composition is ±20 percent of the in-vivo bioavailability of the fluoroquinolone determined after an amount of the fluoroquinolone is administered orally to an animal as a tablet The phrase "forms a precipitate," as used herein, means that the pharmaceutical composition forms a precipitate, or solid, when injected into water. A precipitate is an insoluble solid formed in a solvent at room temperature. To determine whether a precipitate forms when the pharmaceutical compositions of the invention are combined with water, a volume of the pharmaceutical composition, for example, 50 µL, is injected into a given volume of water, for example, 5 mL, to provide an aqueous mixture and the aqueous mixture is then filtered. If less than 10% by weight of the pharmaceutical composition is retained on a 0.22 µm filter when the aqueous mixture is filtered at room temperature, i.e., about 22° C., the pharmaceutical composition is said not to form a precipitate when injected into water.

The phrase "treating," "treatment of," and the like, as used herein, include the amelioration or cessation of a specified condition.

The phrase "preventing," "prevention of," and the like, as used herein, include the avoidance of the onset of a condition.

The term "condition," as used herein means an interruption, cessation, or disorder of a bodily function, system, or organ.

The term "animal," as used herein, includes, but is not limited to, humans, canines, felines, equines, bovines, ovines, porcines, amphibians, reptiles, and avians. Representative animals include, but are not limited to a cow, a horse, a sheep, a pig, an ungulate, a chimpanzee, a monkey, a baboon, a chicken, a turkey, a mouse, a rabbit, a rat, a guinea pig, a dog, a cat, and a human.

The term "pharmaceutically acceptable organic solvent," as used herein, means an organic solvent that when administered to an animal does not have undue adverse effects such as excessive toxicity, irritation, or allergic response commensurate with a reasonable benefit/risk ratio.

The term "glycerol," as used herein, means $CH_2(OH)CH(OH)CH_2(OH)$.

The term "propylene glycol," as used herein, means $CH_2(OH)CH_2CH_2(OH)$ or $CH_2(OH)CH_2(OH)CH_3$, i.e., 1,3-propylene glycol or 1,2-propylene glycol.

The term "glycerol formal," as used herein means an organic solvent of formula $C_4H_8O_3$ that exists as a mixture of 5-hydroxy-1,3-dioxane and 4-hydroxymethyl-1,3-dioxolane in a ratio of about 60:40. Although the solvent glycerol formal consists of two chemical compounds, the two chemical compounds being in a specific ratio of about 60:40, it is typically considered a "solvent" rather than a mixture of compounds. This is because the 5-hydroxy-1,3-dioxane and 4-hydroxymethyl-1,3-dioxolane are in equilibrium with each other. Accordingly, the term glycerol formal (i.e., a mixture of 5-hydroxy-1,3-dioxane and 4-hydroxymethyl-1,3-dioxolane in a ratio of about 60:40), as used herein, is an organic solvent.

The term "effective amount," as used herein, means an amount sufficient to treat or prevent a condition in an animal.

The Pharmaceutical Compositions

The pharmaceutical compositions comprise (i) a salt formed between a fluoroquinolone and a carboxylic acid, (ii) a cyclodextrin, and (iii) a pharmaceutically acceptable organic solvent, wherein the pharmaceutical composition is a solution. The carboxylic acid salt of the fluoroquinolone is dissolved in the pharmaceutically acceptable organic solvent to provide a solution of the carboxylic acid salt of a fluoroquinolone in the pharmaceutically acceptable organic solvent.

In one embodiment, the pharmaceutical composition is adapted for oral administration.

In one embodiment, the pharmaceutical composition is adapted for administration by injection.

The invention further relates to a pharmaceutical composition comprising a fluoroquinolone in a solution, wherein the in-vivo bioavailability of the fluoroquinolone determined after an amount of the fluoroquinolone is administered orally to an animal as the pharmaceutical composition is substantially similar to the in-vivo bioavailability of the fluoroquinolone determined after the same amount of the fluoroquinolone is administered orally to an animal as a tablet.

In one embodiment, the in-vivo bioavailability of the fluoroquinolone determined after an amount of the fluoroquinolone is administered orally to an animal as the pharmaceutical composition is ±15 percent of the in-vivo bioavailability of the fluoroquinolone determined after the same amount of the fluoroquinolone is administered orally to an animal as a tablet. In one embodiment, the in-vivo bioavailability of the fluoroquinolone determined after an amount of the fluoroquinolone is administered orally to an animal as the pharmaceutical composition is ±10 percent of the in-vivo bioavailability of the fluoroquinolone determined after the same amount of the fluoroquinolone is administered orally to an animal as a tablet. In one embodiment, the in-vivo bioavailability of the fluoroquinolone determined after an amount of the fluoroquinolone is administered orally to an animal as the pharmaceutical composition is ±5 percent of the in-vivo bioavailability of the fluoroquinolone determined after the same amount of the fluoroquinolone is administered orally to an animal as a tablet.

In one embodiment, the pharmaceutical composition is administered to an animal by injection and the area under the curve ("AUC"), determined from a plot of fluorquinolone concentration in the animal's serum against time, is greater than the area under the curve, determined from a similar plot, when a comparable composition that does not include the cyclodextrin is administered to the animal. One skilled in the art readily knows how to determine AUC. The phrase "comparable composition that does not include the cyclodextrin," as used herein, means a composition that is the same in all respects to the composition that includes the cyclodextrin except that the cyclodextrin is not included in the composition. In one embodiment, the "comparable composition that does not include the cyclodextrin" is made by simply combining the components of the composition, except for the cyclodextrin, in the same amounts and filling to volume with the pharmaceutically acceptable organic solvent to provide a composition. It is recognized that this will result in a composition that differs from the cyclodextrin containing composition in that there will be small differences in, for example, the amount of the solvent and/or the relative ratio of the remaining components of the composition. Such compositions are considered a "comparable composition that does not include the cyclodextrin." In one embodiment, the "comparable composition that does not include the cyclodextrin" is made by replacing the cyclodextran with an equivalent amount of an inert excipient. Such compositions are also considered a "comparable composition that does not include the cyclodextrin."

The Salt Formed Between a Fluoroquinolone and a Carboxylic Acid

The fluoroquinolone can be any fluoroquinolone known to those skilled in the art. Representative fluoroquinolones useful in the compositions and methods of the invention include, but are not limited to, those described in BE 870,576, U.S. Pat. No. 4,448,962, DE 3,142,854, EP 047,005, EP 206,283, BE 887,574, EP 221,463, EP 140,116, EP 131,839, EP 154,780, EP 078,362, EP 310,849, EP 520,240, U.S. Pat. No. 4,499,091, U.S. Pat. No. 4,704,459, U.S. Pat. No. 4,795,751, U.S. Pat. No. 4,668,784, and U.S. Pat. No. 5,532,239, the contents of which are expressly incorporated herein by reference thereto.

Representative fluoroquinolones useful in the compositions and methods of the invention include, but are not limited to, ciprofloxacin (commercially available as Cipro®), enrofloxacin (commercially available as Baytril®), enoxacin (commercially available as Penetrex®), gatifloxacin (commercially available as Tequin®), gemifloxacin (commercially available as Factive®), levofloxacin (commercially available as Levaquin®), lomefloxacin (commercially available as Maxaquin®), moxifloxacin (commercially available as Avelox®), norfloxacin (commercially available as Noroxin®), ofloxacin (commercially available as Floxin®), sparfloxacin (commercially available as Zagam®), trovafloxacin (commercially available as Trovan®), difloxacin, cinofloxacin, pefloxacin, tosufloxacin, temafloxacin, flerofloxacin, amifloxacin, benofloxacin, danofloxacin, flerofloxacin, marbofloxacin, ruflocaxin, and sarafloxacin.

In one embodiment, the fluoroquinolone is ciprofloxacin.
In one embodiment, the fluoroquinolone is enrofloxacin.
In one embodiment, the fluoroquinolone is gatifloxacin.
In one embodiment, the fluoroquinolone is gemifloxacin.
In one embodiment, the fluoroquinolone is levofloxacin.
In one embodiment, the fluoroquinolone is lomefloxacin.
In one embodiment, the fluoroquinolone is moxifloxacin.
In one embodiment, the fluoroquinolone is ofloxacin.
In one embodiment, the fluoroquinolone is sparfloxacin.
In one embodiment, the fluoroquinolone is trovafloxacin.
In one embodiment, the fluoroquinolone is difloxacin.
In one embodiment, the fluoroquinolone is cinofloxacin.
In one embodiment, the fluoroquinolone is pefloxacin.
In one embodiment, the fluoroquinolone is tosufloxacin.
In one embodiment, the fluoroquinolone is temafloxacin.
In one embodiment, the fluoroquinolone is flerofloxacin.
In one embodiment, the fluoroquinolone is amifloxacin.
In one embodiment, the fluoroquinolone is benofloxacin.
In one embodiment, the fluoroquinolone is danofloxacin.
In one embodiment, the fluoroquinolone is flerofloxacin.
In one embodiment, the fluoroquinolone is marbofloxacin.
In one embodiment, the fluoroquinolone is ruflocaxin.
In one embodiment, the fluoroquinolone is sarafloxacin.

Any carboxylic acid of formula R—C(O)OH, wherein R is a $C_1$-$C_4$ hydrocarbon group known to those skilled in the art can be used in the compositions and methods of the invention. Representative carboxylic acids include, but are not limited to butanoic acid, propanoic acid, and acetic acid.

In one embodiment, the R in RC(O)OH is $C_1$-$C_3$ hydrocarbon group.
In one embodiment, the R in RC(O)OH is $C_1$-$C_2$ hydrocarbon group.
In one embodiment, the carboxylic acid is acetic acid.
In one embodiment, the R in RC(O)OH is a $C_1$-$C_4$ hydrocarbon group that is a straight chain hydrocarbon group.
In one embodiment, the R in RC(O)OH is a $C_1$-$C_4$ hydrocarbon group that is a branched chain hydrocarbon group.
In one embodiment, the $C_1$-$C_4$ hydrocarbon group is substituted with an —OH or —$NH_2$ group.

Without wishing to be bound by theory, it is believed that the carboxylic acid protonates an amino nitrogen atom of the fluoroquinolone to provide a protonated fluoroquinolone molecule and a carboxylate anion. The protonated fluoroquinolone molecule and the carboxylate anion interact ionically to form the carboxylic acid salt of a fluoroquinolone.

In one embodiment, the salt formed between a fluoroquinolone and a carboxylic acid is a salt formed from acetic acid and enrofloxacin. In one embodiment, the salt formed between a fluoroquinolone and a carboxylic acid is a salt formed from propionic acid and enrofloxacin. In one embodiment, the salt formed between a fluoroquinolone and a carboxylic acid is a salt formed from butyric acid and enrofloxacin. In one embodiment, the salt formed between a fluoroquinolone and a carboxylic acid is a salt formed from pentanoic acid and enrofloxacin.

Typically, the salt formed between a fluoroquinolone and a carboxylic acid is present in the pharmaceutical composition in an amount ranging from about 0.5 percent to 20 percent by weight of the pharmaceutical composition. In one embodiment, the salt formed between a fluoroquinolone and a carboxylic acid is present in the pharmaceutical composition in an amount ranging from about 0.5 percent to 10 percent by weight of the pharmaceutical composition. In one embodiment, the salt formed between a fluoroquinolone and a carboxylic acid is present in the pharmaceutical composition in an amount ranging from about 0.5 percent to 5 percent by weight of the pharmaceutical composition. In one embodiment, the salt formed between a fluoroquinolone and a carboxylic acid is present in the pharmaceutical composition in an amount ranging from about 1 percent to 4 percent by weight of the pharmaceutical composition. In one embodiment, the salt formed between a fluoroquinolone and a carboxylic acid is present in the pharmaceutical composition in an amount of about 2.3 percent by weight of the pharmaceutical composition. It is possible, however, to prepare pharmaceutical compositions wherein the salt formed between a fluoroquinolone and a carboxylic acid is present in the pharmaceutical composition in an amount of up to about 30 percent by weight of the pharmaceutical composition and even higher. In one embodiment, the salt formed between a fluoroquinolone and a carboxylic acid is present in the pharmaceutical composition in an amount ranging from about 20 percent to 30 percent by weight of the pharmaceutical composition. In addition to the high concentration of fluoroquinolone that is obtainable with the pharmaceutical compositions of the invention, advantageously, the pharmaceutical compositions are typically clear solutions.

The salt formed between a fluoroquinolone and a carboxylic acid can be prepared by simply contacting a fluoroquinolone and a carboxylic acid. Typically, the fluoroquinolone is contacted with the carboxylic acid by dissolving the fluoroquinolone in a suitable solvent to provide a solution and adding at least one equivalent of carboxylic acid per equivalent of fluoroquinolone to the resulting solution. Typically, about 0.9 to 3, preferably about 0.95 to 2.5, more preferably about 1 to 2.3, and most preferably about 1 to 2.1 equivalents of carboxylic acid is used per equivalent of fluoroquinolone. In one embodiment, about 0.9 to 1.2 equivalents of carboxylic acid is used per equivalent of fluoroquinolone. Typically, the carboxylic acid is added to the solution with stirring. Typically, the solvent is at room temperature, however, the solvent can be heated to any temperature up to the boiling point of the solvent, provided that the elevated temperature does not cause decomposition of the fluoroquinolone or the carboxylic acid. Preferably, the solvent dissolves both the fluoroquinolone and the carboxylic acid. Generally, the solvent is an organic solvent. Preferably, the solvent is a non-aqueous solvent.

In one embodiment, the salt formed between a fluoroquinolone and a carboxylic acid is prepared by dissolving a salt, other than a carboxylic acid salt (for example, a hydrochloride salt), of a fluoroquinolone in a solvent to provide a solution; adding at least 2 equivalents of carboxylic acid to the solution; and then separating the resulting carboxylic acid salt of the fluoroquinolone from the solvent. Typically, about 2 to 3, preferably about 2.1 to 3, more preferably about 2.2 to 2.5, and most preferably about 2.2 to 2.3 equivalents of carboxylic acid is used per equivalent of fluoroquinolone. Fluoroquinolones are typically commercially available as the hydrochloride salt or the free base.

After the carboxylic acid is added to the solution, the resulting salt formed between a fluoroquinolone and a carboxylic acid is separated from the solution. In one embodiment, the salt formed between a fluoroquinolone and a carboxylic acid precipitates and is collected by filtration. In another embodiment, the solvent is removed by evaporation, typically under reduced pressure, to provide the salt formed between a fluoroquinolone and a carboxylic acid as a solid.

Suitable solvents useful for preparing the carboxylic acid salt of a fluoroquinolone include, but are not limited to, dichloromethane, methylene chloride, methanol, ethanol, acetone, ethyl acetate, and acetonitrile.

The carboxylic acid salt of a fluoroquinolone can be purified using standard methods known to those skilled in the art including, but not limited to, recrystallization, extraction, and chromatography.

Alternatively, the pharmaceutical composition can be prepared by simply contacting a fluoroquinolone and a carboxylic acid in the pharmaceutically acceptable organic solvent. Typically, about 0.9 to 3, preferably about 0.95 to 2.5, more preferably about 1 to 2.3, and most preferably about 1 to 2.1 equivalents of carboxylic acid is used per equivalent of fluoroquinolone. In one embodiment, about 0.9 to 1.2 equivalents of carboxylic acid is used per equivalent of fluoroquinolone. Typically, the fluoroquinolone is contacted with the carboxylic acid in the pharmaceutically acceptable organic solvent with stirring.

Pharmaceutical composition for injection are typically sterile filtered.

The Cyclodextrin

The cyclodextrin can be any cyclodextrin known to those skilled in the art. For example, the cyclodextrin can be a α-cyclodextrin, β-cyclodextrin, or γ-cyclodextrin. The cyclodextrin can also be a chemically modified cyclodextrin, for example, a cyclodextrin wherein some or all of the hydroxyl groups of the cyclodextrin are chemically modified to replace some or all of the hydroxyl protons with methyl, hydroxypropyl, carboxymethyl, or acetyl groups (for example, the hydroxypropyl β-cyclodextrin TrappsolHPB®, the randomly methylated β-cyclodextrin TrappsolRMB®, or the 2,6 di-O-methylβ-cyclodextrin TrappsolDMB®, each commercially available from CTD, Inc. of High Springs, Fla.).

In one embodiment, the cyclodextrin is α-cyclodextrin.
In one embodiment, the cyclodextrin is β-cyclodextrin.
In one embodiment, the cyclodextrin is γ-cyclodextrin Typically, the cyclodextrin is present in an amount ranging from about 0.05 to 5 molar equivalents per equivalent of the fluoroquinolone. In one embodiment, the cyclodextrin is present in an amount ranging from about 0.1 equivalent to 5 equivalents per equivalent of the fluoroquinolone. In one embodiment, the cyclodextrin is present in an amount ranging from about 0.1 equivalent to 2.5 equivalents per equivalent of the fluoroquinolone. In one embodiment, the cyclodextrin is present in an amount ranging from about 0.1 equivalent to 2 equivalents per equivalent of the fluoroquinolone. In one embodiment, the cyclodextrin is present in an amount ranging from about 0.1 equivalent to 1 equivalents per equivalent of the fluoroquinolone.

The Solvent

Any pharmaceutically acceptable organic solvent that will dissolve the carboxylic acid salt of the fluoroquinolone can be used in the pharmaceutical compositions of the invention. Representative, pharmaceutically acceptable organic solvents include, but are not limited to, pyrrolidone, N-methyl-2-pyrrolidone, polyethylene glycol, propylene glycol, glycerol formal, isosorbid dimethyl ether, ethanol, dimethyl sulfoxide, tetraglycol, tetrahydrofurfuryl alcohol, triacetin, propylene carbonate, dimethyl acetaminde, dimethyl formamide, dimethyl sulfoxide, and combinations thereof. In one embodiment, the pharmaceutically acceptable organic solvent is selected from propylene glycol, glycerol, and mixtures thereof. In one embodiment, the solvent is selected from glycerol formal and mixtures of glycerol formal and propylene glycol.

In one embodiment, the pharmaceutically acceptable organic solvent comprises glycerol. In one embodiment, the pharmaceutically acceptable organic solvent is glycerol.

In one embodiment, the pharmaceutically acceptable organic solvent comprises propylene glycol. In one embodiment, the pharmaceutically acceptable organic solvent is propylene glycol.

In one embodiment, the pharmaceutically acceptable organic solvent comprises propylene glycol and glycerol. In one embodiment, the pharmaceutically acceptable organic solvent is propylene glycol and glycerol.

In one embodiment, the pharmaceutically acceptable organic solvent comprises propylene glycol and glycerol wherein the ratio of glycerol to propylene glycol ranges from about 15:85 to 85:15 (v/v). In one embodiment, the pharmaceutically acceptable organic solvent is propylene glycol and glycerol wherein the ratio of glycerol to propylene glycol is about 80:20 (v/v). In one embodiment, the pharmaceutically acceptable organic solvent comprises propylene glycol and glycerol wherein the ratio of glycerol to propylene glycol ranges from about 20:80 to 80:20 (v/v). In one embodiment, the pharmaceutically acceptable organic solvent is propylene glycol and glycerol wherein the ratio of glycerol to propylene glycol is about 80:20 (v/v). In one embodiment, the pharmaceutically acceptable organic solvent comprises propylene glycol and glycerol wherein the ratio of glycerol to propylene glycol ranges from about 25:75 to 75:25 (v/v). In one embodiment, the pharmaceutically acceptable organic solvent is propylene glycol and glycerol wherein the ratio of glycerol to propylene glycol is about 75:25 (v/v). In one embodiment, the pharmaceutically acceptable organic solvent comprises propylene glycol and glycerol wherein the ratio of glycerol to propylene glycol ranges from about 35:65 to 65:35 (v/v). In one embodiment, the pharmaceutically acceptable organic solvent is propylene glycol and glycerol wherein the ratio of glycerol to propylene glycol is about 65:35 (v/v).

In one embodiment, the pharmaceutically acceptable organic solvent comprises propylene glycol and glycerol wherein the ratio of glycerol to propylene glycol is about 50:50 (v/v). In one embodiment, the pharmaceutically acceptable organic solvent is propylene glycol and glycerol wherein the ratio of glycerol to propylene glycol is about 50:50 (v/v).

Pharmaceutical compositions wherein the solvent comprises glycerol and/or propylene glycol are advantageous, especially in veterinary applications, because the compositions, when administered orally to an animal, become sticky when introduced into the oral cavity and are difficult for the animal to spit. Accordingly, the animal is more likely to swallow the formulation, resulting in easier administration.

In one embodiment, the solvent comprises glycerol formal. In one embodiment, the solvent is glycerol formal.

In one embodiment, the pharmaceutically acceptable organic solvent comprises propylene glycol and glycerol formal wherein the ratio of glycerol formal to propylene glycol ranges from about 15:85 to 85:15 (v/v). In one embodiment, the pharmaceutically acceptable organic solvent comprises propylene glycol and glycerol formal wherein the ratio of glycerol formal to propylene glycol ranges from about 20:80 to 80:20 (v/v). In one embodiment, the pharmaceutically acceptable organic solvent is propylene glycol and glycerol wherein the ratio of glycerol formal to propylene glycol is about 80:20 (v/v). In one embodiment, the pharmaceutically acceptable organic solvent comprises propylene glycol and glycerol formal wherein the ratio of glycerol formal to propylene glycol ranges from about 25:75 to 75:25 (v/v). In one embodiment, the pharmaceutically acceptable organic solvent is propylene glycol and glycerol formal wherein the ratio of glycerol formal to propylene glycol is about 75:25 (v/v). In one embodiment, the pharmaceutically acceptable organic solvent comprises propylene glycol and glycerol formal wherein the ratio of glycerol formal to propylene glycol ranges from about 35:65 to 65:35 (v/v). In one embodiment, the pharmaceutically acceptable organic solvent is propylene glycol and glycerol formal wherein the ratio of glycerol formal to propylene glycol is about 65:35 (v/v).

In one embodiment, the pharmaceutical composition of the invention is substantially free of water.

In one embodiment, the pharmaceutical composition of the invention has less than about 2 percent by weight of water. In one embodiment, the pharmaceutical composition of the invention has less than about 1 percent by weight of water. In one embodiment, the pharmaceutical composition of the invention has less than about 0.5 percent by weight of water. In one embodiment, the pharmaceutical composition of the invention has less than about 0.2 percent by weight of water.

The solution of the salt formed between a fluoroquinolone and a carboxylic acid in the pharmaceutically acceptable organic solvent is prepared by simply adding the salt formed between a fluoroquinolone and a carboxylic acid and the cyclodextrin to the pharmaceutically acceptable organic solvent and stirring or agitating the resulting mixture. For example, the mixture can be agitated using a vortex mixture.

By using organic solvents, it is possible to provide pharmaceutical compositions wherein the concentration of the fluoroquinolone is much higher than is obtainable with aqueous formulations. Also, by using organic solvents, it is possible to provide pharmaceutical compositions wherein the concentration of the cyclodextrin is much higher than is obtainable with aqueous formulations. Cyclodextrins, typically have a low solubility in aqueous solvents.

Indeed, by using organic solvents it is possible to provide pharmaceutical compositions that allow a therapeutically effective dose of the fluoroquinolone to be orally administered to an animal in a relatively small volume. Typically, a therapeutically effective dose of the fluoroquinolone can be orally administered to the animal in a solvent volume of about 1 mL or less. The liquid oral pharmaceutical compositions of the invention are advantageous because they are easier to administer to some patient populations, such as pediatric patients, who find it difficult to swallow solid oral pharmaceutical compositions. Similarly, the liquid oral pharmaceutical compositions of the invention are advantageous in veterinary medicine because of the difficulty in administering solid oral pharmaceutical compositions to some animals, such as cats.

The much higher concentration of the fluoroquinolone obtained by using organic solvents rather than aqueous solvents also permits pharmaceutical compositions that are suitable for injection. Indeed, by using organic solvents it is possible to provide pharmaceutical compositions that allow a therapeutically effective dose of the fluoroquinolone to be administered to an animal by injection in a relatively small volume. Indeed, a therapeutically effective dose of the fluoroquinolone can often be administered to the animal by injecting a solvent volume of about 1 mL or less.

Without wishing to be bound by theory, it is believed that the presence of the cyclodextrin in the pharmaceutical composition decreases the rate of absorption of the fluoroquinolone, compared to a pharmaceutical composition that does not include the cyclodextrin, when the pharmaceutical composition of the invention is administered orally to an animal. Without wishing to be bound by theory, it is also believed that the presence of the cyclodextrin in the pharmaceutical composition decreases the rate of elimination of the fluoroquinolone, compared to a pharmaceutical composition that does not include the cyclodextrin, when the pharmaceutical composition of the invention is orally administered to an animal. Thus, the pharmacokinetics of orally administering a fluoroquinolone as a pharmaceutical composition of the invention is more similar to the pharmacokinetics of administering a fluoroquinolone as a tablet (which typically has slower absorption and slower elimination than a liquid formulation) compared to a liquid pharmaceutical composition that does not include the cyclodextrin. Without wishing to be bound by theory, it is believed that the effects of the cyclodextrin are due to the formation of an inclusion complex with the salt formed between a fluoroquinolone and a carboxylic acid.

Similarly, without wishing to be bound by theory, it is believed that administering the pharmaceutical composition by injection provides a greater area under the curve (AUC), compared to a formulation that does not include the cyclodextrin, because of greater bioavailability and a slower rate of elimination.

The pharmaceutical compositions of the invention advantageously do not form a solid precipitate when administered orally or by injection. The pharmaceutical compositions of the invention do not form a precipitate when injected into water. In one embodiment, the pharmaceutical compositions of the invention do not form a precipitate when about 50 µL of the pharmaceutical composition is injected into about 5 mL of water. In one embodiment, the pharmaceutical compositions of the invention do not form a precipitate when about 0.1 mL of the pharmaceutical composition is injected into about 5 mL of water. In one embodiment, the pharmaceutical compositions of the invention do not form a precipitate when about 0.25 of the pharmaceutical composition is injected into about 5 mL of water. In one embodiment, the pharmaceutical compositions of the invention do not form a precipitate when about 1 mL of the pharmaceutical composition is injected into about 5 mL of water.

Other Excipients

The pharmaceutical compositions, in particular those for oral administration, can further comprise one or more pharmaceutically acceptable excipients. Suitable pharmaceutically acceptable excipients include, but are not limited to, sweeteners, flavoring agents, preservatives, and coloring agents. Such excipients are known in the art. Examples of suitable pharmaceutical excipients are described in Remington's Pharmaceutical Sciences 1447-1676 (Alfonso R. Gennaro ed., 19th ed. 1995), the contents of which are incorporated herein by reference.

Examples of sweeteners are any natural or artificial sweetener, such as fructose, sucrose, xylitol, sodium saccharin, cyclamate, aspartame, and acsulfame.

Examples of flavoring agents are Magnasweet (trademark of MAFCO); oil of wintergreen; bubble gum flavor; peppermint flavor; spearmint flavor; fruit flavors such as cherry, grape, and orange; fish flavor such as tuna; and the like. Sweeteners and flavoring agents are useful to provide a more palatable preparation.

Examples of preservatives are potassium sorbate, methylparaben, propylparaben, benzoic acid and its salts, esters of parahydroxybenzoic acid such as butylparaben, alcohols such as ethyl or benzyl alcohol, phenolic compounds such as phenol, and quaternary ammonium compounds such as benzalkonium chloride.

Methods of Treating or Preventing a Condition in an Animal

The invention further relates to methods of treating or preventing a condition in an animal comprising orally administering to an animal in need thereof an effective amount of a pharmaceutical composition of the invention.

In one embodiment, the invention relates to methods of treating a condition in an animal comprising orally administering to an animal in need thereof an effective amount of a pharmaceutical composition of the invention.

In one embodiment, the invention relates to methods of preventing a condition in an animal comprising orally administering to an animal in need thereof an effective amount of a pharmaceutical composition of the invention.

The invention further relates to methods of treating or preventing a condition in an animal comprising administering to an animal in need thereof an effective amount of a pharmaceutical composition of the invention by injection.

In one embodiment, the invention relates to methods of treating a condition in an animal comprising administering to an animal in need thereof an effective amount of a pharmaceutical composition of the invention by injection.

In one embodiment, the invention relates to methods of preventing a condition in an animal comprising administering to an animal in need thereof an effective amount of a pharmaceutical composition of the invention by injection.

In one embodiment, the animal is a mammal.
In one embodiment, the animal is a canine, a feline, an equine, a bovine, an ovine, or a porcine.
In one embodiment the animal is a human.
In one embodiment, the animal is a non-human animal.
In one embodiment, the animal is a dog.
In one embodiment, the animal is a cat.
In one embodiment, the animal is a cow.
In one embodiment, the animal is a pig.
In one embodiment, the animal is a horse.
In one embodiment, the animal is a sheep.
In one embodiment, the animal is a monkey.
In one embodiment, the animal is a baboon.
In one embodiment, the animal is a rat.
In one embodiment, the animal is a mouse.
In one embodiment, the animal is a guinea pig.

Representative conditions that can be treated or prevented with the methods of the invention include, but are not limited to, bacterial infections and nephrotic syndromes (such as those disclosed in U.S. Pat. No. 5,532,239, the contents of which are expressly incorporated herein by reference thereto).

In one embodiment, the condition is a bacterial infection.
In one embodiment, the condition is a bacterial infection caused by *Staphylococcus aureus, Streptococcus pneumoniae,* coagulese-negative *staphylococci, Streptococcus pyogenes, Staphylococcus epidermis, Pseudomonas aeruginosa, Escherichia coli, Klebsiella pneumoniae, Enterobacter cloacae, Proteus mirabilis, Proteus vulgaris, Providencia stuartii, Morganella morganii, Citrobacter diversus, Citrobacter freundii, Haemophilus influenzae,* or *Neisseria gonorrhea.*

In one embodiment, the condition is a respiratory tract infection, a urinary tract infection, a postoperative-wound infection, a bone or joint infection, a skin infection, an ear infection, or a sexually transmitted disease.

In one embodiment, the condition is a nephrotic syndrome.

The effective amount administered to the animal depends on a variety of factors including, but not limited to the type of animal being treated, the condition being treated, the severity of the condition, and the specific fluoroquinolone being administered. One of ordinary skill in the art will readily know what is an effective amount of the pharmaceutical composition to treat a condition in an animal. For example when the fatty acid salt of a fluoroquinolone is a fatty acid salt of ciprofloxacin, the condition is a bacterial infection, and the animal is a dog, an effective amount is typically between about 2.5 and 10 mg of ciprofloxacin/lb (between about 5 and 30 mg of ciprofloxacin/kg) administered orally once a day or two times per day until 2-3 days after cessation of the condition. When the fatty acid salt of a fluoroquinolone is a fatty acid salt of ciprofloxacin, the condition is a bacterial infection, and the animal is a cat, an effective amount is typically not more than 5 mg of fluoroquinolone/kg administered orally once a day until 2-3 days after cessation of the condition.

In one embodiment, the effective amount of the pharmaceutical composition is administered orally once per day until 2-3 days after cessation of the condition.

In one embodiment, the effective amount of the pharmaceutical composition is administered orally as two doses per day until 2-3 days after cessation of the condition.

In one embodiment, effective amount of the pharmaceutical composition is administered orally once per day for 7 days.

In one embodiment, the effective amount of the pharmaceutical composition is administered orally as two doses per day for 7 days.

In one embodiment, the effective amount of the pharmaceutical composition is administered orally once per day for 14 days.

In one embodiment, the effective amount of the pharmaceutical composition is administered orally as two doses per day for 14 days.

In one embodiment, the effective amount of the pharmaceutical composition is administered orally once per day for 21 days.

In one embodiment, the effective amount of the pharmaceutical composition is administered orally as two doses per day for 21 days.

Orally administering a fluoroquinolone as a pharmaceutical composition of the invention can be easier than administering a solid oral dosage form, such as a capsule or tablet, especially when the animal is a non-human animal. Similarly, administering a fluoroquinolone as a pharmaceutical composition of the invention is easier than administering a fluoroquinolone parenterally.

In various situations, however, parenteral administration can be preferred. Administration by injection, includes, but is not limited to, intradermal; intramuscular; intraperitoneal; intravenous; and subcutaneous.

Typically, when an effective amount of the pharmaceutical composition of the invention is administered to an animal by injection it is administered at a doses ranging from about 1 mg/kg/day to 30 mg/kg/day. In one embodiment, an effective amount of the pharmaceutical composition of the invention is administered to an animal by injection at a dose ranging from about 1 mg/kg/day to about 15 mg/kg/day. In one embodiment, an effective amount of the pharmaceutical composition of the invention is administered to an animal by injection at a dose ranging from about 5 mg/kg/day to about 15 mg/kg/day. In one embodiment, an effective amount of the pharmaceutical composition of the invention is administered to an animal by injection at a dose ranging from about 7.5 mg/kg/day to about 12.5 mg/kg/day. In one embodiment, an effective amount of the pharmaceutical composition of the invention is administered to an animal by injection at a dose ranging from about 3 to 7 mg/kg/day. In one embodiment, an effective amount of the pharmaceutical composition of the invention is administered to an animal by injection at a dose ranging from about 6 to 9 mg/kg/day. In one embodiment, an effective amount of the pharmaceutical composition of the invention is administered to an animal by injection at a dose ranging from about 8 to 12 mg/kg/day. In one embodiment, an effective amount of the pharmaceutical composition of the invention is administered to an animal by injection at a dose of about 20 mg/kg/day. In one embodiment, an effective amount of the pharmaceutical composition of the invention is administered to an animal by injection at a dose of about 10 mg/kg/day. In one embodiment, an effective amount of the pharmaceutical composition of the invention is administered to an animal by injection at a dose of about 7.5 mg/kg/day. In one embodiment, an effective amount of the pharmaceutical composition of the invention is administered to an animal by injection at a dose of about 5 mg/kg/day.

In one embodiment, an effective amount of the pharmaceutical composition of the invention is administered to an animal by injection once a day until the injection subsides. In one embodiment, an effective amount of the pharmaceutical composition of the invention is administered to an animal by injection every other day until the injection subsides.

In one embodiment, an effective amount of the pharmaceutical composition of the invention is administered to an animal by injection once a day for about 7 days. In one embodiment, an effective amount of the pharmaceutical composition of the invention is administered to an animal by injection every other day for about 8 days.

In one embodiment, an effective amount of the pharmaceutical composition of the invention is administered to an animal by injection once a day for about 14 days. In one embodiment, an effective amount of the pharmaceutical composition of the invention is administered to an animal by injection every other day for about 14 days.

In one embodiment, a single injection of an effective amount of the pharmaceutical composition of the invention is administered to an animal.

In one embodiment, a single injection of an effective amount of the pharmaceutical composition of the invention is administered to an animal followed by orally administering to the animal an effective amount of a pharmaceutical composition of the invention. The effective amount administered orally can, for example, be administered by any of the oral administration regimens described above.

The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

EXAMPLES

Example 1

Oral Pharmaceutical Composition of Enrofloxacin—Acetic Acid Salt and Cyclodextrin 2.3 gr of enrofloxacin ($6.4 \times 10^{-3}$ moles) and 1.07 mL ($1.9 \times 10^{-2}$ moles) of acetic acid were combined with 50 ml of propylene glycol in a 100 ml volumetric flask to provide a suspension. The suspension was sonicated occasionally and mixed on a shaker to provide a clear solution. 7.27 g of β-cyclodextrin (commercially available from Sigma-Aldrich of Milwaukee, Wis.) was added to the flask and glycerol was added to provide a volume of about 75 mL. The resulting mixture was sonicated occasionally and mixed on a shaker to provide a clear solution. The resulting clear solution was filled to a volume of 100 mL with glycerol and mixed well to provide a clear solution. The concentration of enrofloxacin in the resulting composition is about 23 mg/mL.

Example 2

Oral Pharmaceutical Composition of Enrofloxacin—Butyric Acid Salt and Cyclodextrin A pharmaceutical composition was prepared following a procedure similar to that described in Example 1 except that 1.6 mL of butyric acid ($1.7 \times 10^{-2}$ moles) was used in place of acetic acid.

Example 3

Oral Pharmaceutical Composition of Enrofloxacin—Propionic Acid Salt and Cyclodextrin A pharmaceutical composition was prepared following a procedure similar to that described in Example 1 except that 1.284 mL of propionic acid ($1.7 \times 10^{-2}$ moles) was used in place of acetic acid.

Example 4

Administration of Oral Enrofloxacin to Cats

A cat was orally administered 1 mL of the pharmaceutical composition of Example 1. Another cat was orally administered a tablet of commercially available enrofloxacin (Baytril®, commercially available from Bayer Health Care of Shawnee Mission, Kans., 22.7 mg per tablet). For each cat, the concentration of enrofloxacin in serum was determined as a function of time over a period of about 24 hours. Blood samples were obtained as a function of time and frozen.

For analysis of the blood samples the following procedure was followed:
1) Thaw sample completely and mix well;
2) Transfer 200 µl of the sample into a microfuge tube;
3) Add 400 µl of methanol and mix well;
4) Centrifuge at 13,000 rpm, −9° C. for 15 minutes;
5) Transfer the supernatant to a 20 mL scintillation vial and add 3,400 µl of mobile phase A (described below);
6) Mix well, filter using a Acrodisc 13 mm syringe filter with 0.2 µm membrane and analyze by HPLC using the following conditions:
   Column: Waters X Bridge C-18 4.6 mm×50 mm column equipped with a Gemini 4 mm×3 mm guard cartridge.
   Injection Volume: 20 µL
   Flow Rate: 2 mL/min., isochratic 85% mobile phase A 15% mobile phase B
   Mobile Phase:
      Composition:
         A: 100 mM phosphate buffer—pH 2.1
         B: Methanol
   Acquisition Wavelength: 274 nm
      Fluorescence: Excitation: 297 nm
         Emission: 440 nm
         Gain 1000
         Attenuation: 4
   Run time: 10 min.

At the end of each analysis, the column is washed with 90 percent aqueous methanol.

Mobile phase A can be prepared by the following procedure:
1. Weigh 13.8 g of sodium phosphate monobasic monohydrate into a 1 liter beaker.
2. Add 500 mL of de-ionized water with stirring.
3. Adjust the pH to 2.11 with phosphoric acid.
4. Transfer the resulting solution into a 1 liter volumetric flask and fill with water to the mark and mix well.

The concentration of enrofloxacin was determined by comparing the enrofloxacin peak area obtained from HPLC analysis of the sample to a standard curve of peak area versus concentration of enrofloxacin obtained by HPLC analysis of several samples of known enrofloxacin concentration.

The standard curve was obtained by weighing 100 mg of commercially available enrofloxacin into a 100 mL volumetric flask and filling the flask to 100 mL with methanol to provide a 1 mg/mL enrofloxacin stock solution. The 1 mg/mL enrofloxacin stock solution was then diluted with methanol to provide various standards by adding 5 mL of the 1 mg/mL enrofloxacin stock solution to 500 mL of methanol to provide a 10 µg/mL standard, adding 0.25 mL of the 1 mg/mL enrofloxacin stock solution to 100 mL of methanol to provide a 0.025 µg/mL standard, adding 0.5 mL of the 1 mg/mL enrofloxacin stock solution to 100 mL of methanol to provide a 0.05 µg/mL standard, adding 1 mL of the 1 mg/mL enrofloxacin stock solution to 100 mL of methanol to provide a 0.1 µg/mL standard, adding 3 mL of the 1 mg/mL enrofloxacin stock solution to 100 mL of methanol to provide a 0.3 µg/mL standard, adding 7 mL of the 1 mg/mL enrofloxacin stock solution to 100 mL of methanol to provide a 0.70 µg/mL standard, adding 15 mL of the 1 mg/mL enrofloxacin stock solution to 100 mL of methanol to provide a 1.5 µg/mL standard.

200 µL of blank serum was then placed in each of four microfuge tubes labeled standard for points 1, 2, 3, and 4. To the tubes labeled standard for points 1, 2, 3, and 4 was then added 200 µL of the 0.025 µg/mL standard, 0.05 µg/mL standard, 0.1 µg/mL standard, 0.3 µg/mL standard, respectively. 200 µL of methanol was then added to each of the tubes; the resulting mixtures mixed with a vortex mixture for about 20 seconds; and then centrifuged at 13,000 rpm at −9° C. for 15 minutes. The resulting supernatant of each sample was then transferred to individual 20 mL scintillation vial and 1400 mL of mobile phase A was added to each supernatant. Each resulting solution was then mixed well, filtered using a Acrodisc 13 mm syringe filter with 0.2 µm membrane and analyze by HPLC using the HPLC method described above to provide the standard curve.

Figure 1:
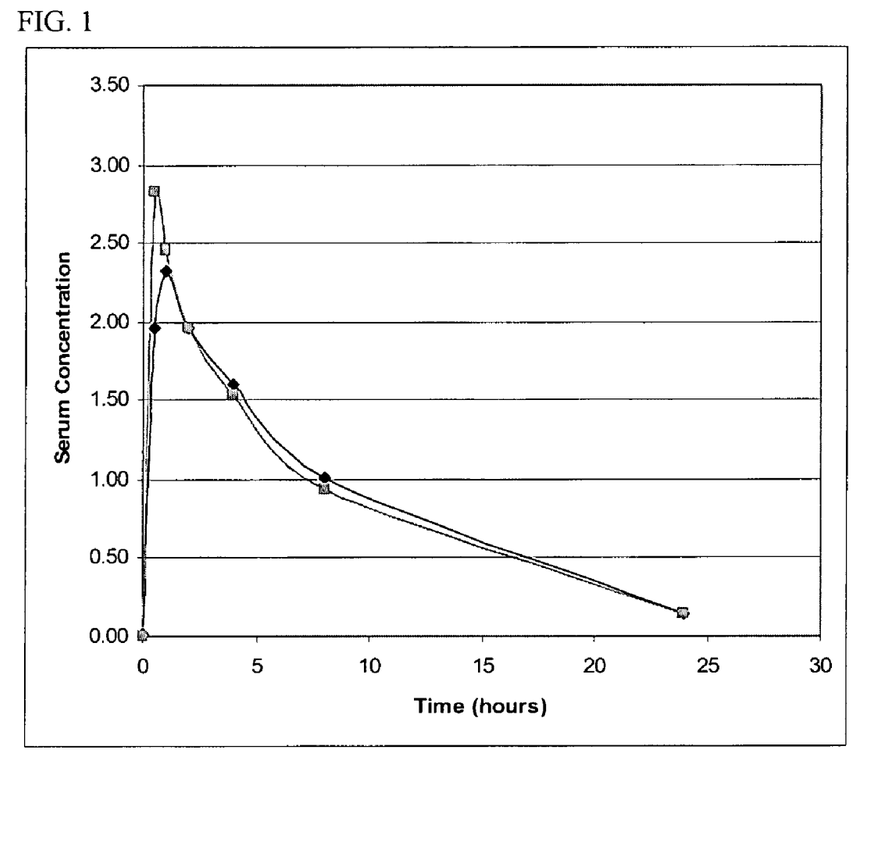
FIG. 1 is a graphical representation of the concentration of enrofloxacin in the serum as a function of time after oral administration to a cat the enrofloxacin pharmaceutical composition of Example 1 (■) and a tablet of commercially available enrofloxacin (Baytril®, commercially available from Bayer Health Care of Shawnee Mission, Kans., 22.7 mg per tablet) (♦). Serum concentration of enrofloxacin is in µg/mL and time is in hours.

FIG. 1 is a graphical representation of the concentration of enrofloxacin in serum in µg/mL as a function of time for each cat. The symbol (♦) represents data points for administration of the solid dosage form of commercially available enrofloxacin (i.e., Baytril®) and the symbol (■) represents data points for administration of enrofloxacin as the liquid pharmaceutical formulation of the invention. The data demonstrates that the oral liquid formulation is bioavailable and that the pharmacokinetic parameters of the oral liquid formulation are similar to that of the solid oral dosage form.

Example 5

Stability of the Pharmaceutical Compositions

The pharmaceutical composition of Example 1 was stored at 70° C. (humidity not controlled) and analyzed daily by the following procedure"

A standard containing 100 mg of enrofloxacin is prepared by:
1. Weigh 100 mg of enrofloxacin into a 100 mL volumetric flask;

2. Add 5 mL methanol and about 50 mL 100 mM phosphate buffer pH 2.11 (prepared as described above for mobile phase A), mix well, and sonicate for about 1 minute to dissolve solids;

3. Fill the flask to 100 mL with 100 mM phosphate buffer pH 2.11 to provide Dilution 1;

4. Transfer 25 mL of Dilution 1 into a 50 mL volumetric flask, add 100 mM phosphate buffer pH 2.11 to a volume of 50 mL, and mix well to provide Dilution 2;

5. Filter a portion of Dilution 2 into an HPLC vial using an Acrodisc 13 mm syringe filter with 0.2 µm membrane;

6. Repeat steps 1-5 two more times to obtain three standards;

7. Analyze each standard by HPLC using the following conditions:

Column: Waters X Bridge C-18 4.6 mm×50 mm column equipped with a Gemini 4 mm×3 mm guard cartridge.
Injection Volume: 10 µL
Flow Rate: 2 mL/min., isochratic 85% mobile phase A 15% mobile phase B
Mobile Phase:
  Composition:
    A: 100 mM phosphate buffer—pH 2.1
    B: Methanol
Acquisition Wavelength: 274 nm
Run time: 10 min.

At the end of each analysis, the column is washed with 90 percent aqueous methanol.

8. Average the peak area obtained for each standard to provide an averaged peak area for the standard The pharmaceutical composition of Example 1 was then analyzed by the following procedure to provide the amount of enrofloxacin in the pharmaceutical composition at time 0:

1. Weigh 40-120 mg of the pharmaceutical composition into a 20 mL scintillation vial;

2. Add 5 mL of 100 mM phosphate buffer pH 2.11 (prepared as described above for mobile phase A) and shake well 3. Filter a portion of this solution using an Acrodisc 13 mm syringe filter with 0.2 µm membrane into an HPLC vial to provide a time 0 sample;

4. Repeat steps 1-3 twice to obtain a total of three time 0 samples;

5. Analyze each time 0 sample by HPLC using the conditions described above;

6. Average the peak areas for each of the time zero samples to provide an averaged peak area for the time 0 sample;

7. Compare the averaged peak area for the time 0 sample to the averaged peak area for the standard averaged standards to obtain the actual amount of enrofloxacin in the pharmaceutical composition.

At various time points, t, a sample of the pharmaceutical composition of Example 1 stored at 70° C. is removed and analyzed following the procedure used to determine the amount of enrofloxacin as time 0 except that a single sample, rather than 3 samples, is analyzed. The peak area obtained by HPLC analysis for the time t sample is then compared to the averaged peak area for the time 0 sample to determine the percent of enrofloxacin in the time t sample relative to the time 0 sample.

The table provided below provides the percent enrofloxacin compared to time 0 as a function of time for the pharmaceutical composition of Example 1 after storage at 70° C.

| Time (days) | Percent Enrofloxacin |
| --- | --- |
| 1 | 99.6 |
| 2 | 99.9 |
| 3 | 99.7 |
| 4 | 99.4 |
| 5 | 99.0 |
| 6 | 99.8 |
| 7 | 98.9 |
| 8 | 97.7 |
| 9 | 98.3 |
| 10 | 98.6 |

The results show that the pharmaceutical compositions of the invention have excellent stability. Typically, the pharmaceutical compositions of the invention show less than a 5 percent decrease in the amount of the fluoroquinolone after being stored at 70° C. for 10 days. In one embodiment, the pharmaceutical compositions of the invention show less than a 4 percent decrease in the amount of the fluoroquinolone after being stored at 70° C. for 10 days. In one embodiment, the pharmaceutical compositions of the invention show less than a 3 percent decrease in the amount of the fluoroquinolone after being stored at 70° C. for 10 days.

Example 6

Subcutaneous Administration of Enrofloxacin to Cats

An injectable composition containing enrofloxacin acetic acid salt and β-cyclodextrin was prepared as described in Example 1. The compositions was sterile filtered to provide an injectable composition.

Figure 2:
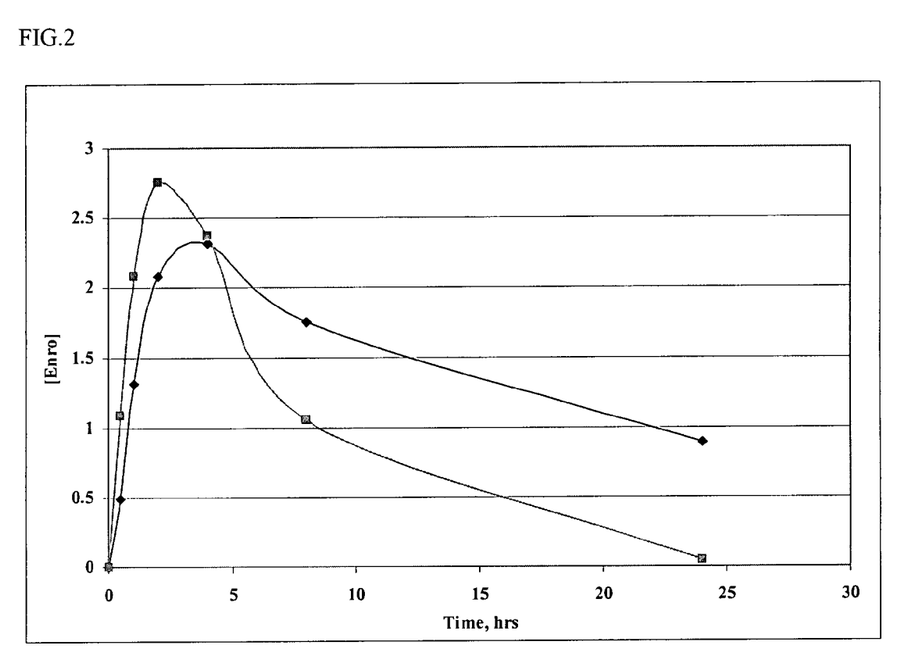
FIG. 2 is a graphical representation of the concentration of enrofloxacin in the serum as a function of time after subcutaneous administration to a cat the enrofloxacin pharmaceutical composition of Example 6 (♦) and commercially available enrofloxacin for injection (Baytril® Injection, commercially available from Bayer Health Care of Shawnee Mission, Kans.) (■). Enrofloxacin was administered at a dose of 5 mg/kg. Serum concentration of enrofloxacin is in µg/mL and time is in hours.

Each of three cats was administered commercially available enroflokacin for injection (Baytril® Injection, commercially available from Bayer Health Care of Shawnee Mission, Kans.) at a dose of 5 mg/kg by subcutaneous injection. To each of three other cats was administered the injectable enrofloxacin composition described in the previous paragraph at a dose of 5 mg/kg by subcutaneous injection. For each cat, the concentration of enrofloxacin in serum was determined as a function of time over a period of about 24 hours using the method described above in Example 4. FIG. 2 is a graphical representation of the concentration of enrofloxacin in serum as a function of time. Each data point represents the serum concentration of enrofloxacin in µg/mL. Each data point represents the average of the serum concentration for the three cats. The symbol (♦) represents data points for administration of the injectable enrofloxacin composition of the invention and the symbol (■) represents data points for administration of commercially available enrofloxacin for injection (i.e., Baytril® Injection).

The data demonstrates that the injectable composition of the invention is bioavailable and that the bioavailability, as measured by area under the curve, is similar to, and in fact better than, the bioavailability of Baytril® Injection. The results show that administering enrofloxacin as an injectable composition of the invention provides a similar or improved bioavailability compared to Baytril® Injection. In particular, we note that the injectable composition of the invention provides a higher serum concentration of enrofloxacin at later time points. For example, at the 24 hour time point, the serum concentration of enrofloxacin in the cats administered the injectable composition of the invention is almost 1 µg/mL whereas in cats administered Baytril® Injection the serum concentration is almost 0 µg/mL. Furthermore, the injectable compositions of the invention provide a lower $C_{max}$ compared to Baytril® Injection. The injectable compositions of the invention, by providing a lower $C_{max}$, can be administered at higher doses than Baytril® Injection and, therefore, provide a therapeutically effective level of enrofloxacin for a longer period of time than can be obtained with Baytril® Injection.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosure of which are incorporated herein by reference.

The invention claimed is:

1. A method of treating a bacterial infection in an animal comprising administering to the animal by injection an effective amount of a pharmaceutical composition comprising (i) a salt formed between a fluoroquinolone and an unsubstituted $C_1$-$C_4$ carboxylic acid, (ii) a cyclodextrin, and (iii) a pharmaceutically acceptable organic solvent, wherein the pharmaceutical composition is a solution and is substantially free of water.

2. The method of claim 1, wherein the bacterial infection is caused by *Staphylococcus aureus, Streptococcus pneumoniae*, coagulese-negative *staphylococci, Streptococcus pyogenes, Staphylococcus epidermis, Pseudomonas aeruginosa, Escherichia coli, Klebsiella pneumoniae, Enterobacter cloacae, Proteus mirabilis, Proteus vulgaris, Providencia stuartii, Morganella morganii, Citrobacter diversus, Citrobacter freundii, Haemophilus influenzae,* and *Neisseria gonorrhea*.

3. The method of claim 1, wherein the bacterial infection is selected from the group consisting of a respiratory tract infection, a urinary tract infection, a postoperative-wound infection, a bone infection, a joint infection, a skin infection, an ear infection, and a sexually transmitted disease.

4. The method of claim 1, wherein the animal is selected from the group consisting of canines, felines, equines, bovines, ovines, porcines, amphibians, reptiles, and avians.

5. The method of claim 1, wherein the animal is selected from the group consisting of a cow, a horse, a sheep, a pig, an ungulate, a chimpanzee, a monkey, a baboon, a chicken, a turkey, a mouse, a rabbit, a rat, a guinea pig, a dog, a cat, and a human.

6. The method of claim 4, wherein the animal is a feline.

7. The method of claim 4, wherein the animal is a canine.

8. The method of claim 1, wherein the effective amount is administered at a dose ranging from about 1 mg/kg/day to about 30 mg/kg/day.

9. The method of claim 1, wherein the method provides an area under the curve, determined from a plot of fluoroquinolone concentration in the animal's serum against time, that is greater than the area under the curve, determined from a similar plot, when a comparable composition that does not include the cyclodextrin is administered to the animal.

10. The method of claim 1, wherein the salt formed between a fluoroquinolone and a carboxylic acid is a salt formed between a carboxylic acid and a fluoroquinolone selected from the group consisting of ciprofloxacin, enrofloxacin, enoxacin, gatifloxacin, gemifloxacin, levofloxacin, lomefloxacin, moxifloxacin, norfloxacin, ofloxacin, sparfloxacin, trovafloxacin, difloxacin, cinofloxacin, pefloxacin, tosufloxacin, temafloxacin, flerofloxacin, amifloxacin, benofloxacin, danofloxacin, flerofloxacin, marbofloxacin, ruflocaxin, and sarafloxacin.

11. The method of claim 1, wherein the salt formed between a fluoroquinolone and a carboxylic acid is a carboxylic acid salt formed between a fluoroquinolone and acetic acid.

12. The method of claim 1, wherein the pharmaceutically acceptable organic solvent is selected from the group consisting of glycerol, propylene glycol, and mixtures of thereof.

13. The method of claim 12, wherein the pharmaceutically acceptable organic solvent is a mixture of glycerol and propylene glycol.

14. The method of claim 13, wherein the ratio of glycerol to propylene glycol ranges from about 85:15 to 15:85.

15. The method of claim 1, wherein the pharmaceutically acceptable organic solvent is selected from the group consisting of glycerol formal, propylene glycol, and mixtures of thereof.

16. The method of claim 15, wherein the pharmaceutically acceptable organic solvent is a mixture of glycerol formal and propylene glycol.

17. The method of claim 16, wherein the ratio of glycerol formal to propylene glycol ranges from about 85:15 to 15:85.

18. The method of claim 1, wherein the carboxylic acid salt of a fluoroquinolone is present in an amount ranging from about 0.5 percent to 20 percent by weight of the pharmaceutical composition.

19. The method of claim 1, wherein the cyclodextrin is β-cyclodextrin.

20. The method of claim 1, wherein the cyclodextrin is α-cyclodextrin.

21. The method of claim 1, wherein the cyclodextrin is γ-cyclodextrin.

22. The method of claim 1, wherein the salt formed between a fluoroquinolone and a carboxylic acid is a salt formed between enrofloxacin and acetic acid.

23. The method of claim 22, wherein the solvent is a mixture of propylene glycol and glycerol.

\* \* \* \* \*